(12) United States Patent
Ishida et al.

(10) Patent No.: US 7,885,377 B2
(45) Date of Patent: Feb. 8, 2011

(54) X-RAY COMPUTER TOMOGRAPHIC APPARATUS, MEDICAL IMAGING APPARATUS, AND MEDICAL IMAGE DISPLAY APPARATUS

(75) Inventors: Fujimaro Ishida, Yokkaichi (JP); Masahiro Ozaki, Otawara (JP); Masatoshi Kanou, Iwakura (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 309 days.

(21) Appl. No.: 11/875,314

(22) Filed: Oct. 19, 2007

(65) Prior Publication Data

US 2008/0095307 A1   Apr. 24, 2008

(30) Foreign Application Priority Data

Oct. 23, 2006   (JP)   ............................. 2006-287949

(51) Int. Cl.
  *A61B 6/00*   (2006.01)
(52) U.S. Cl. ............................................. 378/15; 378/4
(58) Field of Classification Search .................... 378/4, 378/8, 15
  See application file for complete search history.

(56) References Cited

U.S. PATENT DOCUMENTS

| | | | | |
|---|---|---|---|---|
| 5,262,946 | A * | 11/1993 | Heuscher | 378/15 |
| 6,298,111 | B1 * | 10/2001 | Ozaki | 378/8 |
| 6,307,910 | B1 * | 10/2001 | Acharya et al. | 378/4 |
| 6,324,247 | B1 * | 11/2001 | Besson | 378/15 |
| 6,466,638 | B1 * | 10/2002 | Silver et al. | 378/4 |
| 6,778,630 | B2 * | 8/2004 | Silver et al. | 378/15 |
| 7,403,588 | B2 * | 7/2008 | Bruder et al. | 378/9 |
| 2002/0181645 | A1 * | 12/2002 | Bruder et al. | 378/8 |
| 2003/0007593 | A1 * | 1/2003 | Heuscher et al. | 378/4 |
| 2004/0017881 | A1 * | 1/2004 | Cesmeli et al. | 378/4 |
| 2004/0076265 | A1 * | 4/2004 | Heuscher et al. | 378/210 |

(Continued)

FOREIGN PATENT DOCUMENTS

CN   1638696 A   7/2005

(Continued)

OTHER PUBLICATIONS

Office Action issued Sep. 2, 2010, in Chinese Patent Application 200710167403.5 (with English Translation), 18 pages.

*Primary Examiner*—Edward J Glick
*Assistant Examiner*—Alexander H Taningco
(74) *Attorney, Agent, or Firm*—Oblon, Spivak, McClelland, Maier & Neustadt, L.L.P.

(57) ABSTRACT

An X-ray computed tomographic apparatus includes an X-ray tube, an X-ray detector, a rotating mechanism unit which continuously rotates the X-ray tube around a subject to be examined, together with the X-ray detector, a data storage unit which stores projection data corresponding to an output from the X-ray detector in association with the angles of the X-ray tube at the time of data acquisition, a reconstruction processing unit which reconstructs a plurality of images on the basis of a plurality of projection data sets stored in the data storage unit, the plurality of projection data sets corresponding to the same range from a first view angle to a second view angle, and a display unit which displays the plurality of reconstructed images.

14 Claims, 5 Drawing Sheets

U.S. PATENT DOCUMENTS

| | | | |
|---|---|---|---|
| 2004/0114727 A1* | 6/2004 | Yan et al. | 378/210 |
| 2004/0174960 A1* | 9/2004 | Hsieh et al. | 378/210 |
| 2005/0201509 A1* | 9/2005 | Mostafavi et al. | 378/8 |
| 2008/0101531 A1* | 5/2008 | Seamans et al. | 378/8 |
| 2009/0074133 A1* | 3/2009 | Nielsen et al. | 378/19 |

FOREIGN PATENT DOCUMENTS

JP    2004-173923    6/2004

\* cited by examiner

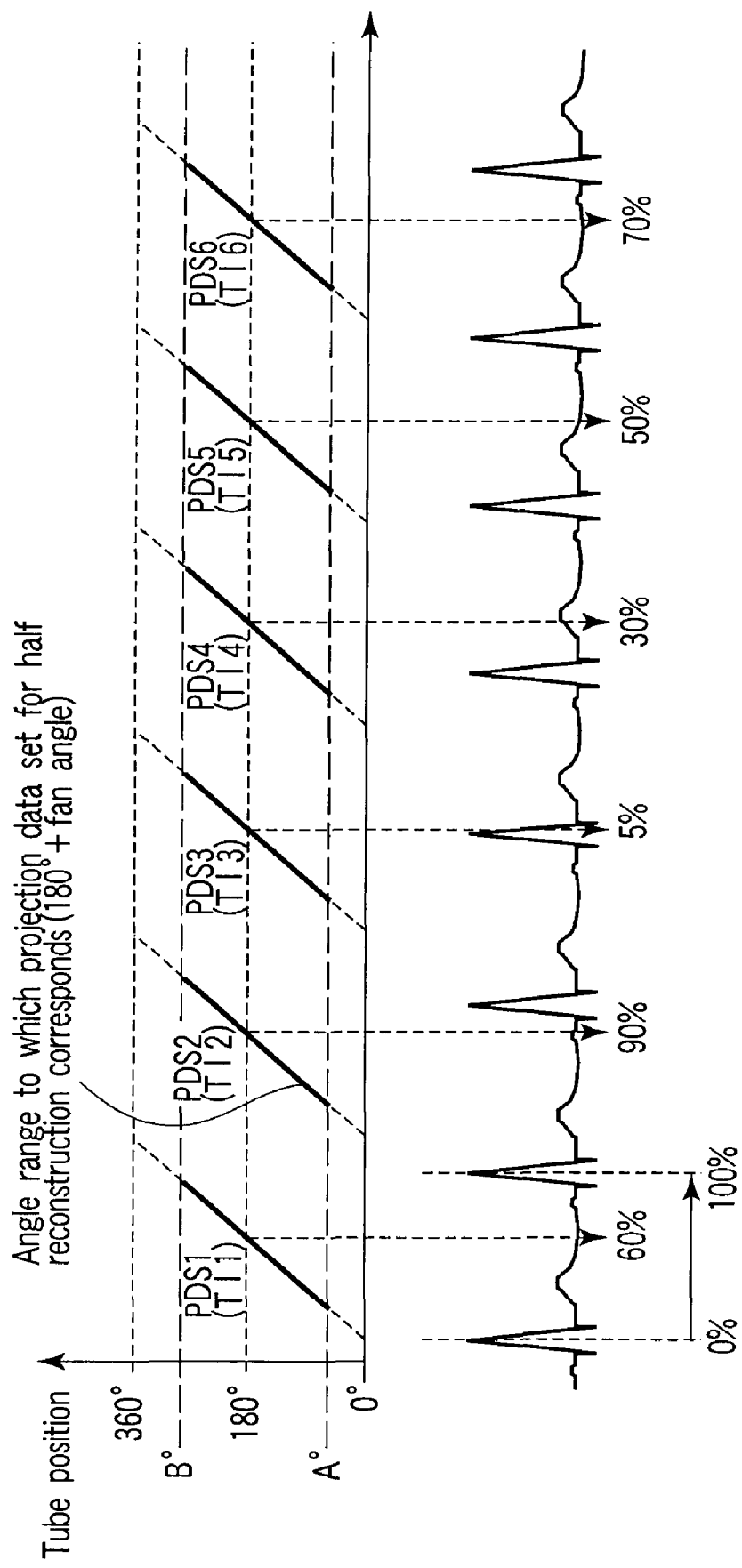
F I G. 5

X-RAY COMPUTER TOMOGRAPHIC APPARATUS, MEDICAL IMAGING APPARATUS, AND MEDICAL IMAGE DISPLAY APPARATUS

CROSS-REFERENCE TO RELATED APPLICATIONS

This application is based upon and claims the benefit of priority from prior Japanese Patent Application No. 2006-287949, filed Oct. 23, 2006, the entire contents of which are incorporated herein by reference.

BACKGROUND OF THE INVENTION

1. Field of the Invention

The present invention relates to an X-ray computed tomographic apparatus which reconstructs an image associated with a slice of a subject to be examined, a medical imaging apparatus, and a medical image display apparatus.

2. Description of the Related Art

Slight periodic blur occurs even on an image captured by imaging a subject to be examined which is completely motionless. This is not because of image noise, but because of slight movement in the subject, which occurs, for example, at a period of 0.4 sec in a 0.4-sec scan. The causes of such blur mainly reside in mechanical variations such as the shake of a gantry due to gravity and centrifugal force and the positional shift of the tube focal position. With such variation, the position of the tube (focal point)/detector deviates from an ideal state in a cycle of 360°, resulting in the occurrence of blur on an image. In image diagnosis using still images, such blur is a level difference which is not recognized by an observer. However, in observation of a completely motionless object through a moving image, the observer recognizes the movement described above.

In an actual clinical practice, examination using an X-ray computed tomographic apparatus is considered effective in evaluating the rupture risk of a cerebral aneurysm. A cerebral aneurysm with a high rupture risk changes its shape with a change in blood pressure. Observation using moving images is therefore effective. Electrocardiographic information is electrical information generated by a change in the state of the cardiac muscle. This information also indicates a change in blood pressure to show the movement of the heart. Clarifying the association between a change in this state and a rupture risk makes it possible to properly determine the urgency of an operation and the like.

BRIEF SUMMARY OF THE INVENTION

It is an object of the present invention to reduce variations in the position of a subject image on a moving image due to mechanical shake and the like which occur upon rotation of a gantry.

According to an aspect of the present invention, there is provided an X-ray computed tomographic apparatus comprising an X-ray tube, an X-ray detector, a rotating mechanism unit which continuously rotates the X-ray tube around a subject to be examined, together with the X-ray detector, a data storage unit which stores projection data corresponding to an output from the X-ray detector in association with angles of the X-ray tube at the time of data acquisition, a reconstruction processing unit which reconstructs a plurality of images on the basis of a plurality of projection data sets stored in the data storage unit, the plurality of projection data sets corresponding to the same range from a first view angle to a second view angle, and a display unit which displays the plurality of reconstructed images.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the preferred embodiments given below, serve to explain the principles of the invention.

FIG. 5 is a timing chart showing other data sets read out for half reconstruction by the data set read control unit in FIG. 1;

DETAILED DESCRIPTION OF THE INVENTION

An embodiment of the present invention will be described below with reference to the views of the accompanying drawing.

Figure 1:
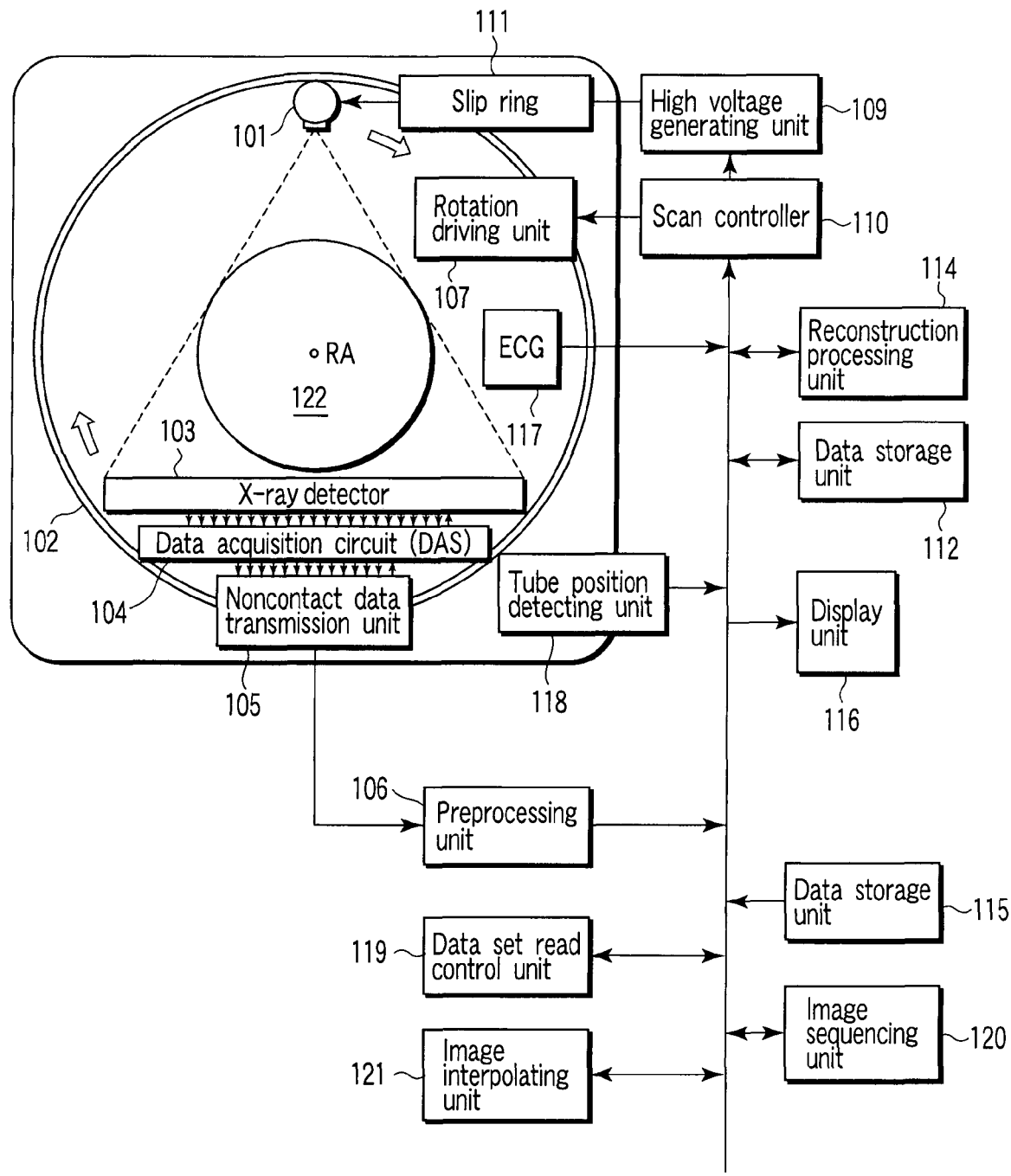
FIG. 1 is a block diagram showing the arrangement of an X-ray computed tomographic apparatus according to an embodiment of the present invention.

FIG. 1 shows the arrangement of an X-ray computed tomographic apparatus according to this embodiment. A gantry 100 includes an X-ray tube 101 and an X-ray detector 103. A high voltage generating unit 109 applies a tube voltage to the X-ray tube 101 through a slip ring 111 and supplies a filament current to the X-ray tube 101. With this operation, the X-ray tube 101 generates X-rays. As the X-ray detector 103, a multi-slice type detector comprising, for example, 256 rows is used. As the X-ray detector 103, a multi-slice type detector comprising another number of rows or a single-slice detector may be used. As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and migration of the electron-hole pairs to an electrode, i.e., a photoconductive phenomenon. As an X-ray detection element of the X-ray detector 103, either of these schemes can be used.

An electrocardiograph (ECG) 117 detects an electrocardiogram representing a temporal change in action potential which reflects the beat of the heart (cardiac motion) as a repetitive biological phenomenon of a subject to be examined, and outputs it as a digital signal (electrocardiographic data). A data storage unit 112 stores electrocardiographic data, i.e., the data of an action potential value at each time, in association with a time code representing the time. Although heartbeat is exemplified as a biological phenomenon of the subject, a breathing motion may be detected as another biological phenomenon.

The X-ray tube 101 and the X-ray detector 103 are mounted on an annular rotating frame 102 which is supported so as to be rotatable around a rotation axis RA. The X-ray detector 103 is placed at a position and in an direction where it faces the X-ray tube 101 through an opening portion 122. The subject placed on a bed top (not shown) is inserted into the opening portion 122. The X-ray detector 103 detects X-rays generated from the X-ray tube 101 and transmitted through the subject.

A rotation driving unit 107 drives the rotating frame 102 to continuously rotate it at a high speed of, for example, 0.4 sec/rotation. A tube position detecting unit 118 is provided to detect the angle of the X-ray tube 101, and typically includes a rotary encoder. The angle of the X-ray tube 101 is typically detected as a displacement angle from a reference angle (0°) at which the X-ray tube 101 is located at the uppermost position. Note that an angle of 180° corresponds to the lowermost position of the X-ray tube 101.

The X-ray detector 103 detects X-rays transmitted through the subject. A data acquisition circuit 104 is generally called a DAS (Data Acquisition System). The data acquisition circuit 104 amplifies a signal read out from the X-ray detector 103 for each channel, and converts it into a digital signal. Data output from the data acquisition circuit 104 reflects the intensity of incident X-rays and is generally called pure raw data. A preprocessing unit 106 performs preprocessing such as logarithmic transformation and sensitivity correction for the pure raw data received from the data acquisition circuit 104 through a noncontact data transmission unit 105 to generate so-called projection data (also called raw data) at a stage immediately before reconstruction processing. The data storage unit 112 stores the projection data, with a time code representing the time of the acquisition of the projection data being associated with data concerning the angle of the X-ray tube 101 at the time of the acquisition of the data. The projection data can be made to correspond to an electrocardiogram with the time code.

A reconstruction processing unit 114 uses a so-called half reconstruction method and can reconstruct the data of an image (a single slice or a multi-slice or volume) on the basis of projection data around the subject (180°+fan angle). For the sake of descriptive convenience, projection data corresponding to (180°+fan angle) will be referred to as a projection data set as a unit. An angular position corresponding to a projection data set indicates the start position, end position, or central position of an angle of (180°+fan angle) required for half reconstruction. Assume that in the following description, this angle corresponds to the central position of an angle of (180°+fan angle).

A data set read control unit 119 accesses the data storage unit 112 to read out a plurality of projection data sets from the stored projection data and supply them to the reconstruction processing unit 114. It suffices if read processing of projection data sets by the data set read control unit 119 is essentially equivalent to the processing of selectively reading out only projection data corresponding to an angle range used for the reconstruction processing. For example, this processing includes the processing of reading out all data, and assigning a weight of 1 to projection data corresponding to an angle range used for the reconstruction processing while assigning a weight of 0 to projection data which falls outside the angle range and is not used for reconstruction so as to avoid the data from contributing to a reconstructed image. For the sake of descriptive convenience, assume that in the following description, read processing of projection data sets by the data set read control unit 119 is the processing of selectively reading out only projection data corresponding to an angle range used for the reconstruction processing.

With regard to a plurality of projection data sets to be read out, an angle width to be covered is equal to an angle of (180°+α) required for half reconstruction. The respective projection data sets correspond to the same angular position. For example, when projection data sets cover an angle range from angle of 0° of the X-ray tube 101 to an angle of (180°+α), an angular position corresponding to each projection data set is (90°+α/2). This angular position is common to all the projection data sets.

The reconstruction processing unit 114 reconstructs the data of a plurality of images on the basis of a plurality of projection data sets. The data storage unit 112 stores the data of the plurality of reconstructed images. An angular position corresponding to projection data sets is initially set to (90°+α/2), which can be changed to an arbitrary angular position by an operator through an operation unit 115.

An image sequencing unit 120 can make a plurality of reconstructed images correspond to electrocardiograms by using time codes regardless of the acquisition times (acquisition order) of the respective images, and sequences the respective images in accordance with cardiac phases where they were acquired. Note that a cardiac phase is typically defined as a position represented in % within the interval from an R wave to the next R wave which is normalized with 100%.

An image interpolating unit 121 generates a sequence of images arrayed at predetermined intervals of 1% or several % from a plurality of images sequenced in accordance with cardiac phases by interpolation processing. A sequence of images generated by interpolation are displayed as a moving image on a display unit 116. Although images are arrayed at 1% intervals by default, the operator can change the intervals to arbitrary intervals through the operation unit 115.

The operation of this embodiment will be described next. The rotating frame 102 is continuously rotated at constant speed under the control of a scan controller 110. In this rotation period, X-rays are continuously generated and are repeatedly read by the X-ray detector 103 at a predetermined period. The data storage unit 112 stores the read data as projection data through the DAS 104, data transmission unit 105, and preprocessing unit 106. It suffices to reduce radiation exposure by applying X-rays to the subject within a limited angle range corresponding to projection data sets while applying no X-rays to the subject outside the angle range. Assume that when the rotating frame 102 is to be rotated a plurality of number of times, it is predicted that projection data sets corresponding to the same cardiac phases as those to which already acquired projection data sets correspond are acquired. In this case, it suffices to reduce radiation exposure by stopping the application of X-rays to the subject in the acquisition period of such projection data. In addition, it suffices to apply continuous X-rays or pulse X-rays. When a scheduled time elapses or a predetermined number of rotations is reached, scanning is terminated, and signal processing to be described below is started.

Figure 2:
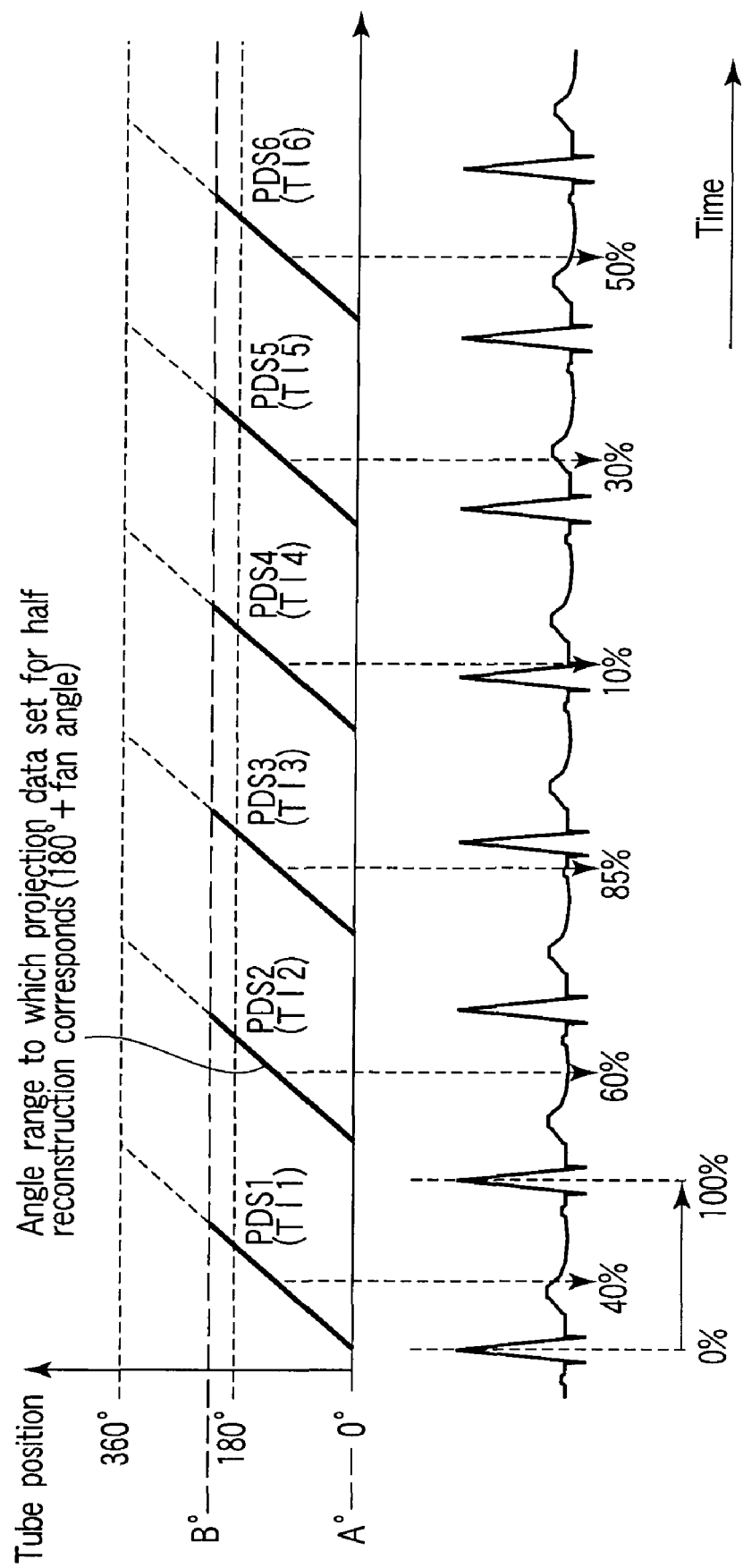
FIG. 2 is a timing chart showing a plurality of data sets read out for half reconstruction by a data set read control unit in FIG. 1.

Referring to FIGS. 2 and 5, the thick lines indicate ranges corresponding to a plurality of projection data sets, which are read out by the data set read control unit 119 in accordance with the tube position and used for half reconstruction, with respect to the path of the X-ray tube 101. Referring to FIG. 2, a projection data set covers the range in which the X-ray tube 101 rotates from a first view angle (A) of 0° to a second view angle (B) of (180°+α). Referring to FIG. 5, a projection data set covers the range in which the X-ray tube 101 rotates from a view angle of (90°−α/2) to a view angle of (270°+α/2). The operator can arbitrarily make the view angles in FIG. 2 or 5 correspond to projection data sets. In addition, the operator can arbitrarily make other angular positions correspond to projection data sets. In either case, it suffices if angular positions to which a plurality of projection data sets correspond are the same. That is, it suffices if a plurality of projection data sets cover the same angle range.

Since the rotation cycle of the X-ray tube 101 is not synchronous with a cardiac cycle, cardiac phases corresponding to the respective projection data sets are indefinite. Referring to FIG. 2, a projection data set PDS1 acquired first corresponds to a cardiac phase of 40%; a projection data set PDS2 acquired second, a cardiac phase of 60%; a projection data set PDS3 acquired third, a cardiac phase of 85%; a projection data set PDS4 acquired fourth, a cardiac phase of 10%; a projection data set PDS5 acquired fifth, a cardiac phase of 30%; and a projection data set PDS6 acquired sixth, a cardiac phase of 50%. Referring to FIG. 5, a projection data set PDS1 acquired first corresponds to a cardiac phase of 60%; a projection data set PDS2 acquired second, a cardiac phase of 90%; a projection data set PDS3 acquired third, a cardiac phase of 5%; a projection data set PDS4 acquired fourth, a cardiac phase of 30%; a projection data set PDS5 acquired fifth, a cardiac phase of 50%; and a projection data set PDS6 acquired sixth, a cardiac phase of 70%.

The reconstruction processing unit 114 reconstructs a plurality of images T11 to T16 on the basis of the plurality of projection data sets PDS1 to PDS6.

The image sequencing unit 120 specifies cardiac phases corresponding to the plurality of reconstructed images T11 to T16. Cardiac phases are specified by collating the electrocardiographic data acquired by scanning and stored in the data storage unit 112 with time codes corresponding to the angular positions of the plurality of projection data sets PDS1 to PDS6 on which the plurality of images T11 to T16 are based.

Figure 3:
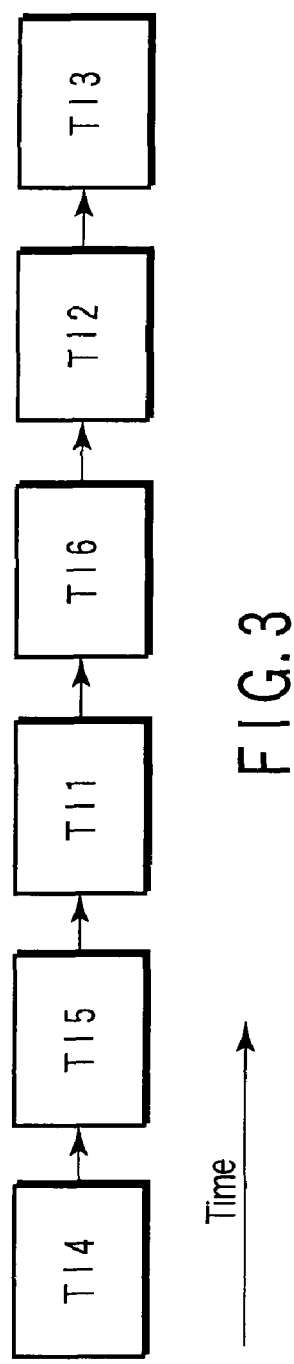
FIG. 3 is a view showing how an image sequencing unit sequences a plurality of images corresponding to the plurality of data sets in FIG. 2.
Figure 4:
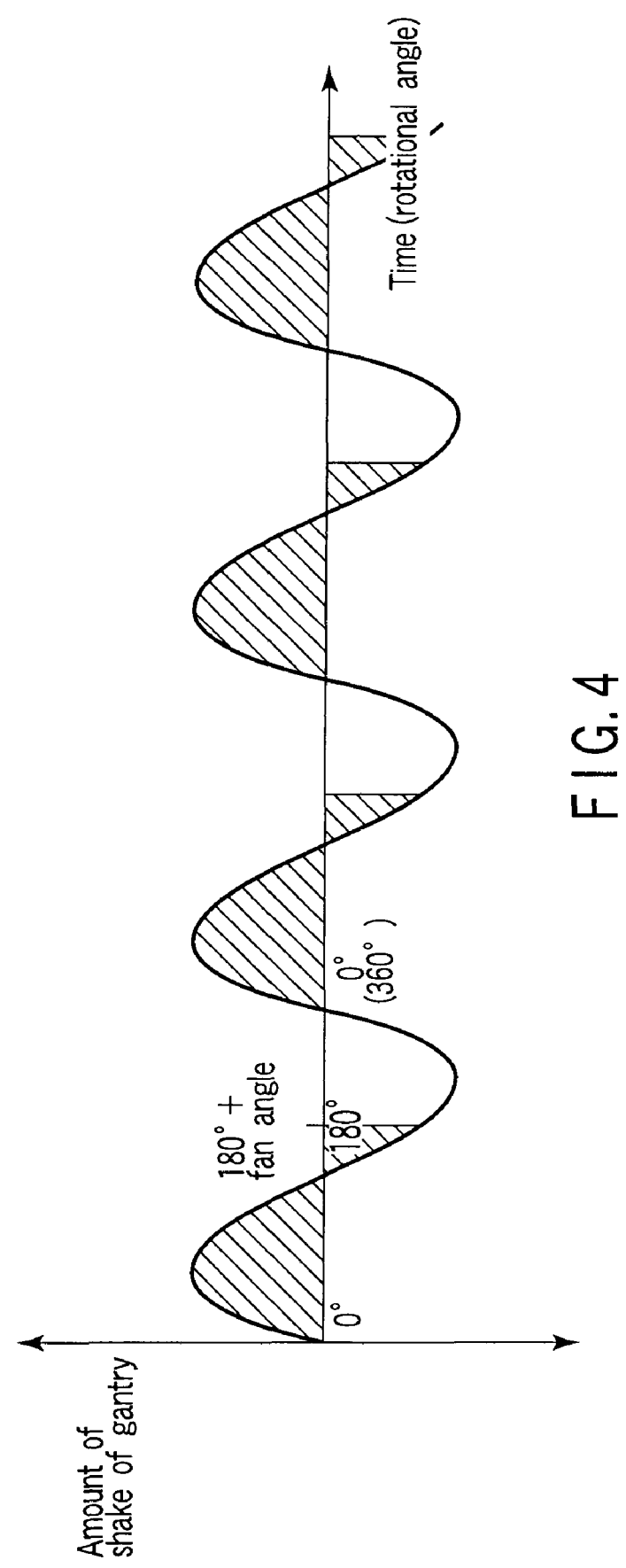
FIG. 4 is a timing chart showing the shake of a gantry which corresponds to each data set in FIG. 2.
Figure 6:
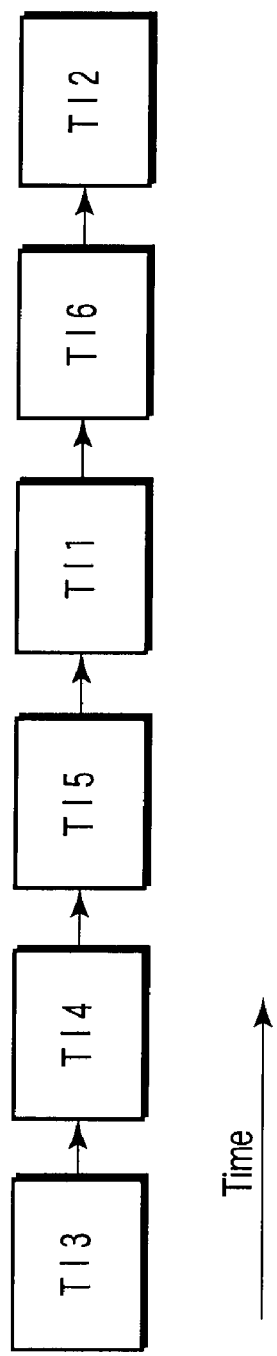
FIG. 6 is a view showing how the image sequencing unit sequences a plurality of images corresponding to the plurality of data sets in FIG. 5.
Figure 7:
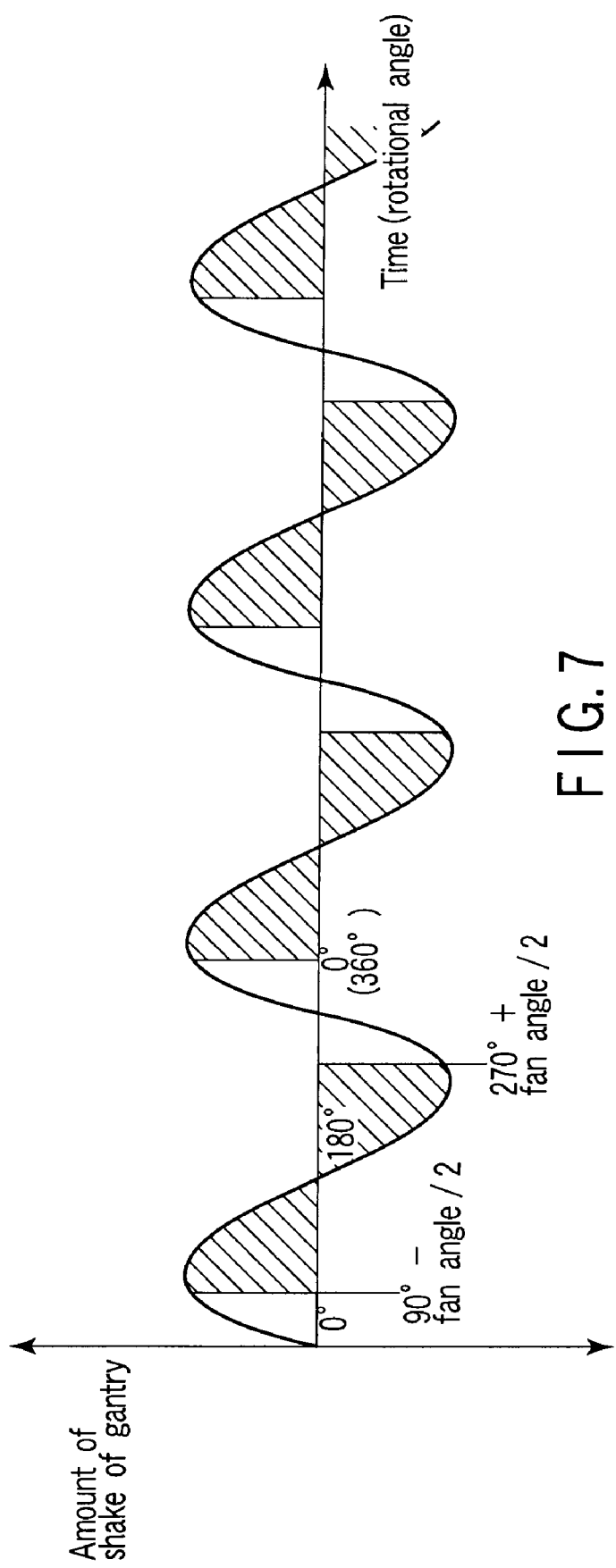
FIG. 7 is a timing chart showing the shake of the gantry which corresponds to each data set in FIG. 5.

The image sequencing unit 120 sequences the plurality of reconstructed images T11 to T16 in accordance with the respective specified cardiac phases. In the case shown in FIG. 2, as shown in FIG. 3, the image T14 corresponding to a cardiac phase of 10%, the image T15 corresponding to a cardiac phase of 30%, the image T11 corresponding to a cardiac phase of 40%, the image T16 corresponding to a cardiac phase of 50%, the image T12 corresponding to a cardiac phase of 60%, and the image T13 corresponding to a cardiac phase of 85% are arranged in the order named. Likewise, in the case shown in FIG. 5, as shown in FIG. 6, the image T13 corresponding to a cardiac phase of 5%, the image T14 corresponding to a cardiac phase of 30%, the image T15 corresponding to a cardiac phase of 50%, the image T11 corresponding to a cardiac phase of 60%, the image T16 corresponding to a cardiac phase of 70%, and the image T12 corresponding to a cardiac phase of 90% are arranged in the order named.

The image interpolating unit 121 generates a sequence of images arranged at equal intervals of 1% or another pitch from the images T11 to T16 sequenced in accordance with the cardiac phases by interpolation processing. The sequence of images generated by interpolation are displayed as a moving image on the display unit 116.

As described above, making angular positions corresponding to a plurality of projection data sets uniform in half reconstruction, i.e., extracting a plurality of projection data sets so as to cover the same angle range within 360°, can make total amounts (hatched portions) of mechanical shake of mainly the rotating frame 102 and the like, which are reflected in a plurality of projection data sets and vary almost periodically along the rotation of the gantry, almost uniform in the plurality of projection data sets (images). Since the position of the subject varies within images due to the total amounts of mechanical shake, making the total amounts of shake uniform makes it possible to fix the position of the subject image within a plurality of images. In other words, the shifts of subject images within the images mainly due to the total amounts of shake can be made uniform in a plurality of images.

In addition, displaying images in an order corresponding to cardiac phases instead of an acquisition order can reproduce the motion of the heart smoothly as a moving image at a high frame rate.

Although the above description has exemplified the dynamic scan system with a fixed scan position, this embodiment can be applied to the helical scan system. In addition, three-dimensional image data (volume data) may be generated from a plurality of images in the same angle range which are reconstructed by the helical scan system, and a CT image representing three-dimensional features in the subject may be generated.

Note that the present invention is not limited to the above embodiments, and constituent elements can be variously modified and embodied at the execution stage within the spirit and scope of the invention. Various inventions can be formed by proper combinations of a plurality of constituent elements disclosed in the above embodiments. For example, several constituent elements may be omitted from the all the constituent elements in each embodiment. In addition, constituent elements of the different embodiments may be combined as needed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomographic apparatus, comprising:
   an X-ray tube configured to generate X-rays;
   an X-ray detector configured to detect X-rays transmitted through a subject to be examined;
   a rotating mechanism unit configured to continuously rotate the X-ray tube around the subject together with the X-ray detector;
   a data storage unit which stores projection data based on an output from the X-ray detector;
   a reconstruction processing unit configured to reconstruct a first image based on a first projection data set, of the projection data stored in the data storage unit, that corresponds to a range from a first view angle to a second view angle, and to reconstruct a second image based on a second projection data set, of the projection data stored in the data storage unit, that was obtained at a different time from that of the first projection data set and that corresponds to the range from the first view angle to the second view angle, wherein the reconstruction processing unit reconstructs the first and second images by a half reconstruction method; and a display unit which displays said reconstructed first and second images.

2. The apparatus according to claim 1, wherein the display unit sequentially displays said reconstructed first and second images in accordance with cardiac phases of the subject.

3. The apparatus according to claim 1, wherein the display unit sequentially displays said reconstructed first and second images in accordance with a periodic biological phenomenon of the subject.

4. The apparatus according to claim 1, wherein the first view angle is A° (A° is an arbitrary angle between 0° to 360°), and the second view angle is (A+(180°+ fan angle)).

5. The apparatus according to claim 1, further comprising a control unit configured to stop applying X-rays to the subject in a range outside an angle range corresponding to said first and second projection data sets.

6. The apparatus according to claim 1, further comprising a modulation unit configured to modulate the X-rays between an angle range corresponding to said first and second projection data sets and a range outside the angle range.

7. The apparatus according to claim 1, wherein the display unit sequentially displays said reconstructed first and second images in an order determined by corresponding first and second cardiac phases, each of the cardiac phases being associated with one of the reconstructed first and second images based on a time period during which the corresponding projection data set was obtained.

8. An X-ray computed tomographic apparatus, comprising:
   an X-ray tube configured to generate X-rays;
   an X-ray detector configured to detect X-rays transmitted through a subject to be examined;
   a rotating mechanism unit configured to continuously rotate the X-ray tube around the subject together with the X-ray detector;
   a reconstruction processing unit configured to reconstruct a first image based on a first projection data set that corresponds to a range from a first view angle to a second view angle, and to reconstruct a second image based on a second projection data set that was obtained at a different time from that of the first projection data set and that corresponds to the range from the first view angle to the second view angle using a half reconstruction method; and
   a display unit which sequentially displays said first and second images in an order determined by corresponding cardiac phases of the subject, each of the first and second images having a corresponding cardiac phase.

9. The apparatus according to claim 8, further comprising a control unit configured to stop applying X-rays to the subject in a range outside the range from the first view angle to the second view angle corresponding to said first and second projection data sets.

10. The apparatus according to claim 8, further comprising a modulation unit configured to modulate the X-rays between the range from the first view angle to the second view angle corresponding to said first and second projection data sets and a range outside the range from the first view angle to the second view angle.

11. A medical imaging apparatus, comprising:
    a data storage unit which stores projection data acquired by continuously rotating an X-ray tube around a subject to be examined, together with an X-ray detector;
    a reconstruction processing unit configured to reconstruct a first image based on a first projection data set, of the projection data stored in the data storage unit, that corresponds to a range from a first view angle to a second view angle, and to reconstruct a second image based on a second projection data set, of the projection data stored in the data storage unit, that was obtained at a different time from that of the first projection data set and that corresponds to the range from the first view angle to the second view angle, wherein the reconstruction processing unit reconstructs the first and second images by a half reconstruction method; and
    a display unit which displays said reconstructed first and second images.

12. The apparatus according to claim 11, wherein the display unit sequentially displays said reconstructed first and second images in accordance with cardiac phases of the subject.

13. The apparatus according to claim 11, wherein the display unit sequentially displays said reconstructed first and second images in accordance with a periodic biological phenomenon of the subject.

14. The apparatus according to claim 11, wherein the first view angle is A° (A° is an arbitrary angle between 0° to 360°), and the second view angle is (A+(180°+ fan angle)).

* * * * *